(12) United States Patent
Carberry et al.

(10) Patent No.: US 8,133,593 B2
(45) Date of Patent: Mar. 13, 2012

(54) PRE-FORM FOR AND METHODS OF FORMING A HOLLOW-CORE SLOTTED PBG OPTICAL FIBER FOR AN ENVIRONMENTAL SENSOR

(75) Inventors: Joel Patrick Carberry, Elmira Heights, NY (US); Leonard Charles Dabich, II, Painted Post, NY (US); Michael Thomas Gallagher, Corning, NY (US); Brett Jason Hoover, Middlebury Center, PA (US); Karl William Koch, III, Elmira, NY (US); Joseph Edward McCarthy, Addison, NY (US)

(73) Assignee: Corning Incorporated, Corning, NY (US)

( * ) Notice: Subject to any disclaimer, the term of this patent is extended or adjusted under 35 U.S.C. 154(b) by 791 days.

(21) Appl. No.: 12/146,928

(22) Filed: Jun. 26, 2008

(65) Prior Publication Data

US 2009/0320526 A1 Dec. 31, 2009

(51) Int. Cl.
*B29B 7/00* (2006.01)
*D02G 3/00* (2006.01)
*B32B 17/06* (2006.01)
*G02B 6/02* (2006.01)

(52) U.S. Cl. ............. 428/542.8; 428/373; 428/375; 428/426; 428/428; 385/123

(58) Field of Classification Search ............ 428/373, 428/375, 542.8, 426, 428; 385/123; 65/125
See application file for complete search history.

(56) References Cited

U.S. PATENT DOCUMENTS

| | | |
|---|---|---|
| 6,243,522 B1 | 6/2001 | Allan et al. |
| 6,444,133 B1 | 9/2002 | Fajardo et al. |
| 6,788,862 B2 | 9/2004 | Aitken et al. |
| 6,847,771 B2 | 1/2005 | Fajardo et al. |
| 6,917,741 B2 | 7/2005 | Fekety et al. |
| 7,343,074 B1 | 3/2008 | Gallagher et al. ............ 385/125 |
| 2003/0230118 A1 | 12/2003 | Dawes et al. |
| 2004/0228592 A1 | 11/2004 | Gaeta et al. |
| 2004/0258381 A1 | 12/2004 | Borrelli et al. |
| 2006/0130528 A1 | 6/2006 | Nelson et al. .................. 65/379 |
| 2007/0266738 A1 | 11/2007 | Gallagher et al. |

OTHER PUBLICATIONS

Wang, Zhaohui Aleck, et al., "A long pathlength liquid-cole waveguide sensor for real-time pCO2 measurements at sea", Marine Chemistry, 84, (2003), pp. 73-84.
Cox, Felicity M., et al., "Opening up optical fibres", Optics Express, Sep. 17, 2007, vol. 15, No. 19, pp. 11843-11848.

*Primary Examiner* — Gwendolyn Blackwell
(74) *Attorney, Agent, or Firm* — Matthew J. Mason (57) ABSTRACT

A preform for forming a hollow-core, slotted photonic bandgap (PBG) optical fiber for use in an environmental sensor, and methods of forming such a fiber using the preform are disclosed. The preform comprises a slotted cladding tube that surrounds a slotted, hollow-core PBG cane. The slots in the cladding tube and PBG cane are longitudinally formed and substantially aligned with each other. When the preform is drawn, the slots merge to form an elongated side opening or slot in the resulting hollow-core PBG fiber.

7 Claims, 8 Drawing Sheets

PRE-FORM FOR AND METHODS OF FORMING A HOLLOW-CORE SLOTTED PBG OPTICAL FIBER FOR AN ENVIRONMENTAL SENSOR

BACKGROUND OF THE INVENTION

1. Field of the Invention

This invention generally relates to methods of forming an optical waveguide for an environmental sensor, and is specifically concerned with a preform for forming a hollow-core, slotted photonic band-gap (PBG) optical fiber for use in an environmental sensor, and methods of forming such a fiber using the preform.

2. Technical Background of the Invention

Environmental sensors in the form of optical fibers having a hollow core are known in the prior art. The hollow core of the fibers used for such sensors typically conducts light by way of a photonic band-gap (PBG) structure surrounding the hollow core. The PBG structure gives rise to a "forbidden frequency range" that corresponds to the wavelength of the light transmitted through the fiber, although hollow core fibers that conduct light via total internal reflection (TIR) for a specific range of wavelengths are also known. Such sensors are used to sense the presence of a "target substance," such as a particular gas or liquid in the ambient environment. The target substance may be, for example, a threshold amount of carbon dioxide in the ambient air that may be indicative of a fire or other hazardous conditions.

In one prior art design, the hollow core of the optical fiber is exposed to the ambient atmosphere at one or both ends of the fiber to allow gases from the ambient atmosphere to continuously flow into the hollow core. In operation, laser light having a wavelength absorbed by the particular gas composition to be detected is continuously conducted through the hollow core of the fiber. When such a gas is introduced into the open end(s) of the fiber from the ambient atmosphere, it begins to flow through the hollow core. The amplitude of the laser light transmitted through the core diminishes because the gas absorbs the light. In the case of the carbon dioxide example referred to earlier, a certain threshold attenuation may be used to generate a signal that triggers a fire alarm circuit.

Such environmental sensors may be used to detect a broad variety of target substances such as different gas compositions in the atmosphere, organic and inorganic particulates or vapor droplets, and even different liquid compositions when the fiber is immersed in a liquid. Such sensors therefore have broad applicability not only as detectors of combustion products or polluting or potentially toxic substances, but also as control or monitoring sensors in industrial manufacturing processes that require the control of the composition of a particular gas or liquid.

An optical waveguide environmental sensor that includes an elongated side opening that directly exposes the hollow core to the ambient environment is disclosed in U.S. Pat. No. 7,343,074, entitled "Optical waveguide environmental sensor and method of manufacture," which patent is commonly assigned and incorporated by reference herein. The elongated side opening forms what is referred to in the art as an "optical ridge waveguide." An optical ridge waveguide typically includes a narrow ridge of material (or materials) that sits on top of a slab of a second (or same) material. A third material of a lower refractive index (often air) surrounds the ridge and the top surface of the slab, thereby providing the refractive guiding mechanism. The slab is typically about the same thickness as the ridge and sits on a substrate of lower refractive index that provides additional vertical confinement.

Optical ridge waveguides are attractive because of their ease of fabrication. The material structure is fabricated in planar layers, and then the waveguide is defined by removing layers of material in selected regions, leaving behind ridges of the original structure. Most ridge waveguides are planar devices that are defined lithographically and then etched using techniques well known in the semiconductor industry. However, it is far more difficult to form such a structure in optical-fiber-based waveguides, particularly in connection with fiber-based environmental sensors that rely on an elongated side opening to expose the hollow core of the fiber to the ambient environment. For example, one way to form an elongated side opening or "slot" in an optical fiber is to use laser machining. Unfortunately, when a laser is used to cut a slot into the fiber, it can adversely affect the strength of the fiber. In addition, forming a long slot using laser machining or mechanical machining is a difficult task.

What is needed, therefore, is a method of forming a hollow-core, slotted PBG optical fiber that does not require machining to form the slot after the fiber is drawn.

SUMMARY OF THE INVENTION

A first aspect of the invention is a preform for forming a slotted photonic band-gap (PBG) optical fiber. The preform includes a cylindrical cladding tube having a first central axis, a front end, a back end, an inner surface that defines an open interior, and an outer surface. The cladding tube has a first longitudinal slot formed in the outer surface through the inner surface and has a front end and a back end. The preform also includes a cane having a second central axis, a PBG region arranged along the second central axis and having a hollow core substantially centered on the second central axis, and a solid outer region surrounding the PBG region and having an outer surface. The cane has a second longitudinal slot formed in the outer surface of the solid region. The cane is disposed within the cladding tube interior, with the first and second central axes substantially aligned and with the first and longitudinal second slots substantially aligned.

A second aspect of the invention is a method of forming a hollow-core, slotted PBG optical fiber. The method includes providing a preform that includes a cladding tube with a first longitudinal slot and that surrounds a cane. The cane has a solid outer region that surrounds a central PBG region having a central hollow core. The cane also has a second longitudinal slot formed in the outer region. The first and second longitudinal slots are substantially aligned. The method also includes drawing the preform to form a hollow-core PBG optical fiber having a longitudinal slot formed therein.

A third aspect of the invention is a method of forming a preform for forming a hollow-core, slotted PBG optical fiber. The method includes providing a cylindrical cladding tube having a first central axis, a front end, a back end, an inner surface that defines an open interior, and an outer surface. The method also includes providing a cane having a second central axis, a PBG region arranged along the second central axis and having a hollow core substantially centered on the second central axis, and a solid outer region having an outer surface and surrounding the PBG region. The method also includes forming a first longitudinal slot in the cladding tube outer surface that extends through the inner surface, and forming a second longitudinal slot in the cane outer surface that extends into the solid outer region. The method also includes disposing the cane in the cladding tube interior with the first and second central axes substantially aligned and with the first and second slots substantially aligned. The method optionally includes using a single slot-forming process to form the first and second slots after disposing the cane in the cladding. The slots can also be formed separately and the cladding and cane combined so that the slots are substantially aligned.

Additional features and advantages of the invention are set forth in the detailed description that follows, and in part will be readily apparent to those skilled in the art from that description or recognized by practicing the invention as described herein, including the detailed description that follows, the claims, as well as the appended drawings. It is to be understood that both the foregoing general description and the following detailed description present exemplary embodiments of the invention, and are intended to provide an overview or framework for understanding the nature and character of the invention as it is claimed. The accompanying drawings are included to provide a further understanding of the invention, and are incorporated into and constitute a part of this specification. The drawings illustrate various embodiments of the invention and, together with the detailed description, serve to explain the principles and operations thereof.

BRIEF DESCRIPTION OF THE DRAWINGS

These and other features, aspects, and advantages of the present invention are better understood when the following detailed description of the invention is read with reference to the accompanying drawings, in which.

DETAILED DESCRIPTION OF THE INVENTION

Reference is now made to preferred embodiments of the invention, examples of which are illustrated in the accompanying drawings. Whenever possible, the same reference numbers and symbols are used throughout the drawings to refer to the same or like parts. In the description below, terms, such as "upper," "lower," "front," "back," "top," "bottom," "vertical," "horizontal," and the like, are relative terms used for the sake of description and are not used in a limiting sense.

The present invention is directed to a preform for and methods of forming a hollow-core photonic band-gap (PBG) optical fiber that includes an elongated opening or "slot" that runs longitudinally along the fiber. The slotted PBG fiber is formed using a slotted preform, and the slot is maintained while drawing the preform into the slotted PBG fiber. This obviates the need to form the slot after the fiber is formed.

Once the preform is formed, the hollow-core, slotted PBG fiber is formed using any one of a number of conventional techniques for forming photonic band-gap fibers. The following commonly owned references relate to forming photonic band-gap optical fibers and are suitable for use with the present invention, and are incorporated by reference herein: U.S. Pat. Nos. 6,243,522, 6,847,771, 6,444,133, 6,788,862, 6,917,741, U.S. Patent Application Publication No. 2004/0258381, U.S. Patent Application Publication No. 2004/0228592, U.S. Patent Application Publication No. 2007/0266738, PCT Patent Application Publication No. WO 01/37008, and U.S. patent application Ser. No. 10/171,335.

Once formed, the hollow-core, slotted PBG fiber can be used to form an optical waveguide environmental sensor as discussed below.

Photonic Band-gap Preform

Figure 1:
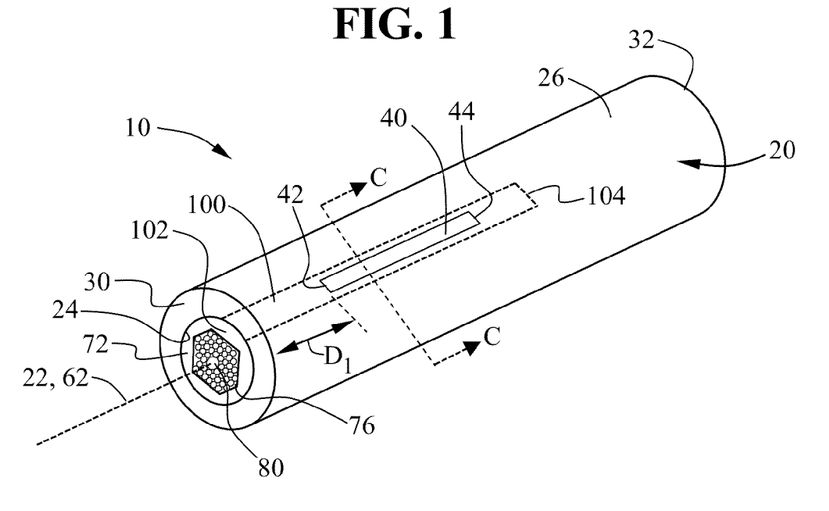
FIG. 1 is a perspective view of an exemplary photonic band-gap (PBG) preform used to form a hollow-core, slotted PBG fiber.
Figure 2:
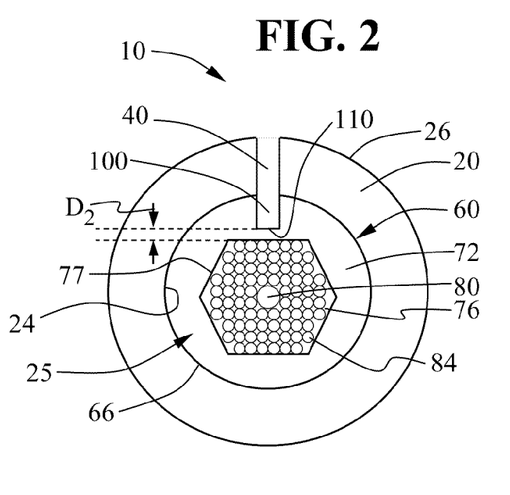
FIG. 2 is a first exemplary cross-sectional view of the PBG preform of FIG. 1, wherein the PBG cane slot does not reach the PBG region.
Figure 3:
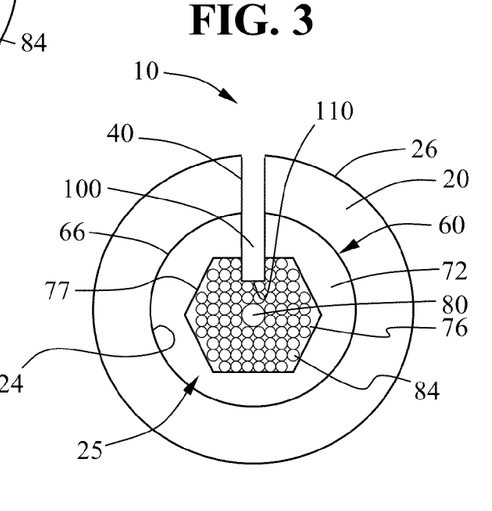
FIG. 3 is a second exemplary cross-sectional view of the PBG preform of FIG. 1, wherein the PBG cane slot extends into the PBG region.
Figure 4:
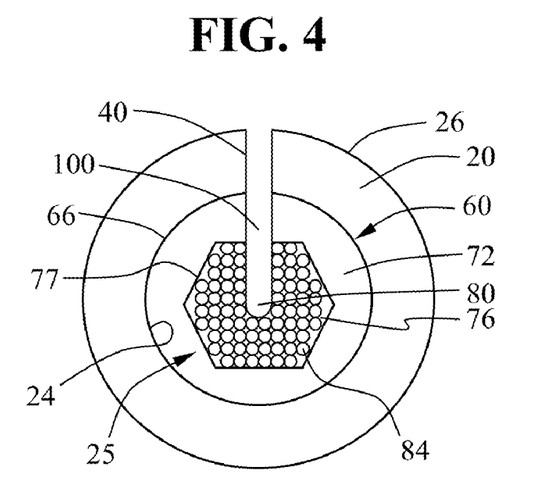
FIG. 4 is a third exemplary cross-sectional view of the PBG preform of FIG. 1, wherein the PBG cane slot extends into the hollow core PBG region.

FIG. 1 is a schematic perspective diagram of an exemplary PBG preform 10 according to the present invention. FIG. 2 through FIG. 4 are first, second and third exemplary cross-sectional views of the exemplary preform taken along the line C-C. Preform 10 includes a cylindrical cladding tube 20 having a central axis 22, an inner surface 24 that defines an interior 25, an outer surface 26, a front end 30 and a back end 32. Cladding tube 20 is made of a material that typically constitutes an optical fiber cladding such as silica.

Cladding tube 20 includes a slot 40 formed in outer surface 26 and that extends through inner surface 24. In an exemplary embodiment, slot 40 is radially oriented. In an alternative embodiment (not shown), slot 40 can be non-radially (i.e., tangentially) oriented. Slot 40 preferably runs longitudinally along cladding tube 20 parallel to central axis 22, and has front and back ends 42 and 44, a width $W_1$, and a length $L_1$. Slot 40 can extend up to 100% of the length of cladding tube 20 such as from about 20% to about 50% of the length of cladding tube 20. In an exemplary embodiment, slot 40 has width $W_1$ in the range from about 0.06 inches to 0.2 inches, and in a particular exemplary embodiment, width $W_1$ is about 0.07 inches. Also in an exemplary embodiment, slot 40 has length $L_1$ in the range from about 4 inches to 8 inches, and in a particular exemplary embodiment, length $L_1$ is about 4 inches. In an exemplary embodiment, slot front end 42 is spaced apart from tube front end 30 by a distance $D_1$. In an exemplary embodiment, distance $D_1$ is in the range from about 1 inch to 2 inches, and in a particular exemplary embodiment, distance $D_1$ is about 1.5 inches.

Figure 5:
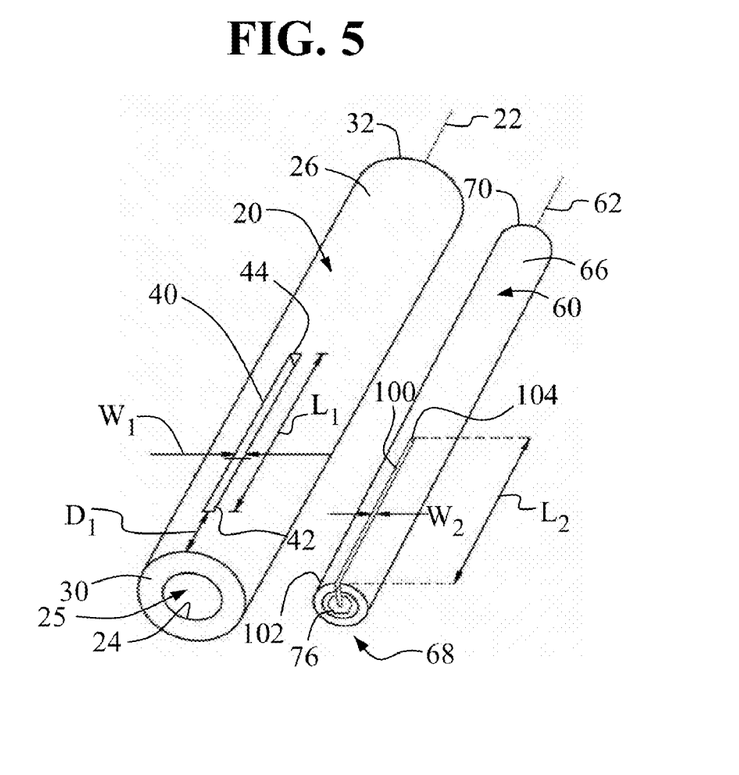
FIG. 5 is a perspective view of the cladding tube and PBG cane prior to combining them to form the preform using one exemplary method wherein the slots are formed prior to disposing the PBG cane in the cladding tube.

Preform 10 also includes a cane 60 that resides in cladding tube interior 25. FIG. 5 is a perspective view of cladding tube 20 and cane 60 prior to combining them to form preform 10. Cane 60 includes a central axis 62, an outer surface 66, a front end 68 and a back end 70. Cane 60 also includes a solid outer region 72 (e.g., silica) that surrounds a PBG region 76 centered on central axis 62 and so is referred to hereinafter as "PBG cane" 60. PBG region 76 comprises a lattice-type microstructure that includes a hollow core 80 located substantially along cane central axis 62. PBG region 76 is configured to create a "band gap" or "forbidden zone" that serves to confine at least one optical mode within hollow core 80. In an exemplary embodiment, PBG region 76 includes one or more "flat sides" 77 such as the hexagonal sides shown in the exemplary cross-section of FIG. 2.

In an exemplary embodiment, PBG region 76 includes a pattern of different light conducting materials having different indexes of refraction such as a pattern of air holes 84. Alternatively, PBG region 76 may be formed from an alternating pattern of two different solid light conducting materials such as two different types of glasses or a glass and a plastic material. PBG region 76 may be formed from alternating layers of such materials, so long as the difference in the indexes of refraction of the two materials effectively creates the aforementioned "forbidden zone."

PBG cane 60 includes a slot 100 formed in outer surface 66 and that extends into cane outer region 72. In an exemplary embodiment, slot 100 is radially oriented. In an alternative embodiment (not shown), slot 100 can be non-radially (i.e., tangentially) oriented. Slot 100 preferably runs longitudinally along cane 60 and has an open front end 102 at cane front end 68, a back end 104, and a bottom 110. Slot 100 has a width $W_2$ and a length $L_2$. In an alternative embodiment (not shown), slot front end 102 can be spaced apart from cane front end 68 at a distance, which can be the same, greater than, or less than distance $D_1$. Slot 100 can extend up to 100% of the length of cane 60 such as from about 20% to about 50% of the length of cane 60. In an exemplary embodiment, slot 100 has width $W_2$ in the range from about 0.06 inches to 0.2 inches, and in a particular exemplary embodiment, width $W_2$ is about 0.07 inches. In respective exemplary embodiments, $W_1 < W_2$, $W_1 > W_2$ and $W_2 \geqq W_1$.

Also in an exemplary embodiment, slot 100 has length $L_2$ in the range from about 4 inches to 8 inches, and in a particular exemplary embodiment, length $L_2$ is about 5.5 inches. In an exemplary embodiment, slot bottom 110 is within cane outer region 72 and is a distance $D_2$ from PBG region 76 as illustrated in FIG. 2, while in another exemplary embodiment, the slot bottom resides within the PBG region as illustrated in FIG. 3. FIG. 4 is a third exemplary cross-sectional view of PBG preform 10 of FIG. 1, wherein the PBG cane slot 100 extends into the hollow core 80, in which case the slot has no bottom 110.

In respective exemplary embodiments, $L_1 < L_2$, $L_1 > L_2$ and $L_1 = L_2$.

Figure 6:
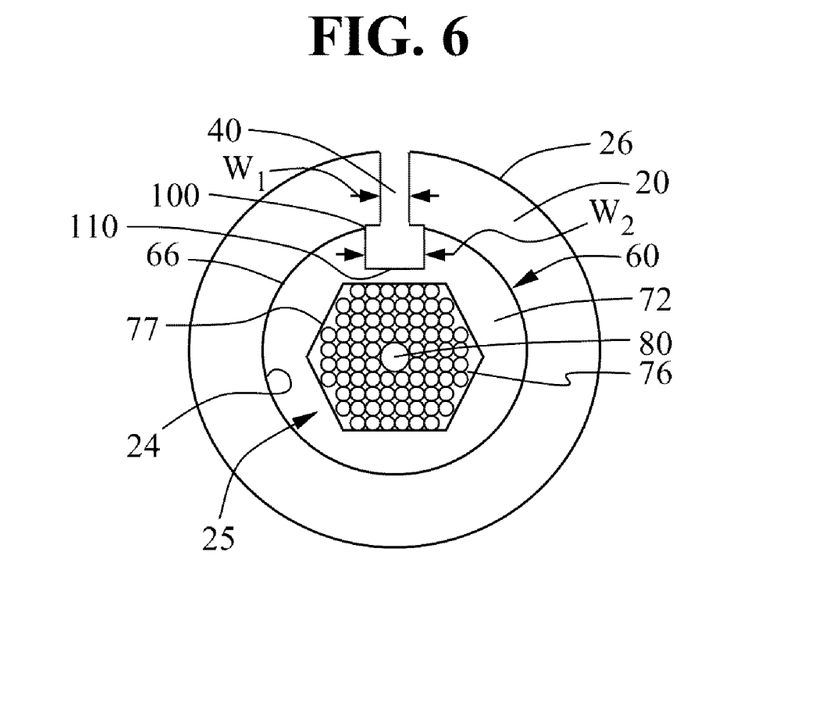
FIG. 6 is a fourth exemplary cross-sectional view of the PBG preform of FIG. 1, wherein the PBG cane slot is wider than the cladding tube slot.

FIG. 6 is a fourth exemplary cross-sectional view of PBG preform 10 of FIG. 1, illustrating an exemplary embodiment wherein cladding slot 40 is narrower than cane slot 100 (e.g., $W_1 = 0.065$ inches and $W_2 = 0.088$ inches). The narrower outer slot 40 reduces heat penetration during the drawing process and also reduces slot deformation and fiber structure deformation.

As shown in FIGS. 1-4 and FIG. 6, preform 10 is formed with PBG cane 60 disposed in interior 25 of cladding tube 20 so that central axes 22 and 62 are substantially aligned. Likewise, cladding slot 40 is substantially aligned with underlying cane slot 100. In an exemplary embodiment, cladding and cane slots 40 and 100 are formed separately, e.g., via separate machining processes, and then PBG cane 60 is disposed in interior 25 of cladding tube 20 and the slots substantially aligned. In another exemplary embodiment, PBG cane 60 is disposed in interior 25 of cladding tube 20, and then both slots 40 and 100 are formed by cutting through the cladding tube and into the PBG cane. In an exemplary embodiment, slots 40 and/or 100 are formed using a machining process such as using a narrow (e.g., 3 mm) diamond-bonded grinding wheel. In addition to grinding, other machining processes, such as etching, milling, lasing, ablating, and/or leaching, may also be used in the formation of slots 40 and/or 100.

Figure 7:
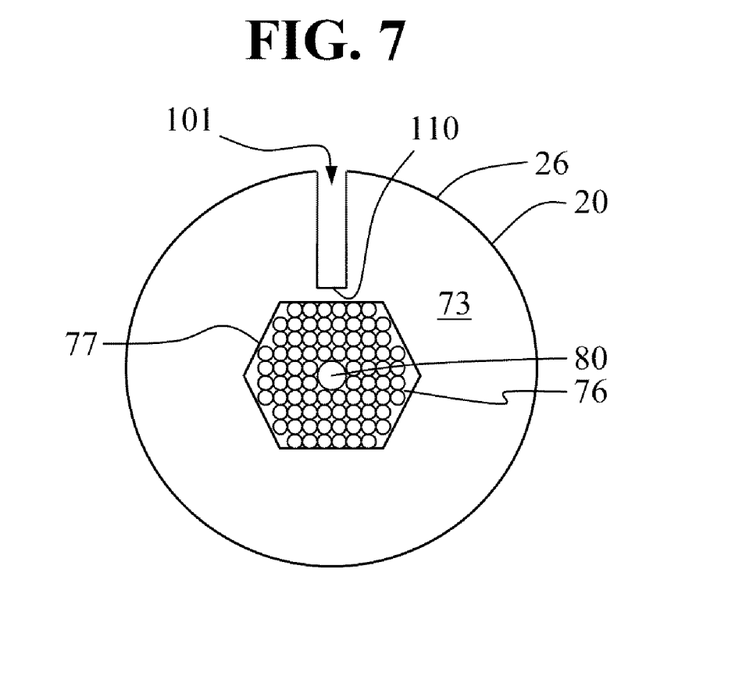
FIG. 7 is a fifth exemplary cross-sectional view of the PBG preform of FIG. 1, wherein the preform is processed to eliminate the interface between the cladding tube and the PBG cane.

Also in an exemplary embodiment illustrated in FIG. 7, PBG preform 10 is processed (e.g., thermally processed) to form a unitary structure that eliminates the interface between cladding tube 20 and PBG cane 60. In the exemplary embodiment, the process includes drawing (or "pre-drawing") PBG preform 10. In the embodiment of FIG. 7, cladding tube 20 merges with PBG cane outer region 72 to form a solid cladding region 73. Solid cladding region 73 can be thought of as a "pre-merged" region since cladding tube 20 and PBG cane outer region 72 merge to form a unitary outer cladding 373 when fiber 202 is drawn, as discussed below. Likewise, cladding tube slot 40 and PBG cane slot 100 merge (or "pre-merge") in the pre-draw process to form a single slot 101 in cladding region 73 (and that optionally extends into PBG region 76).

Drawing Apparatus for Forming Slotted PBG Fiber

Figure 8:
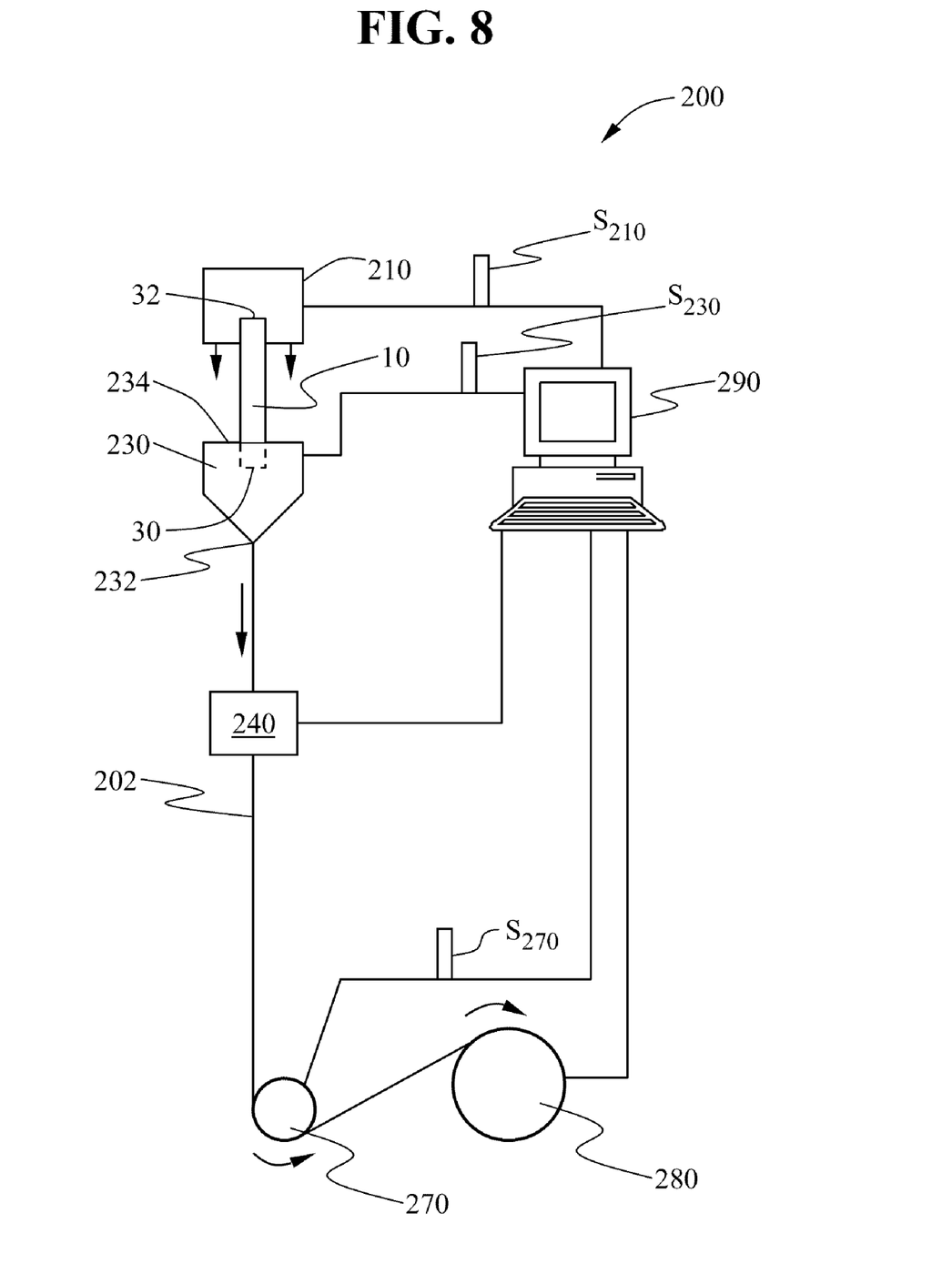
FIG. 8 is schematic diagram of a generalized optical fiber drawing apparatus suitable for forming the hollow-core, slotted PBG fiber from the PBG preform of the present invention.

FIG. 8 is a schematic diagram of a generalized optical fiber drawing apparatus 200 suitable for forming a hollow-core, slotted PBG fiber 202 (hereinafter, "fiber 202") from PBG preform 10 as described above. Fiber 202 is then used to form an optical waveguide environmental sensor as discussed below.

Apparatus 200 includes a feed mechanism 210 that operably engages PBG preform 10, which has front end 30 and back end 32 as described above. Apparatus 200 includes a furnace 230 having an output end 232 and a receiving end 234 arranged to receive preform front end 30 when the feed mechanism is activated. Downstream of furnace 230 is a measuring unit 240 (e.g., a laser micrometer). A pinch wheel 270 is arranged downstream of measuring unit 240, and is arranged to create tension in fiber 202 as the fiber is drawn. Pinch wheel 270 is also arranged to feed fiber 202 to a take-up spool 280. Apparatus 200 further includes a controller 290 operably connected to feed mechanism 210, furnace 230, measuring unit 240, pinch wheel 270, and take-up spool 280.

In operation, PBG preform 10 is placed in apparatus 200 so that feed mechanism 210 engages preform back end 32. In response to a control signal $S_{210}$ from controller 290, feed mechanism 210 introduces preform front end 30 into receiving end 234 of furnace 230. Controller 290 controls a draw temperature of furnace 230 via a furnace control signal $S_{230}$. Furnace 230 acts to soften front end 30, which is then drawn out of furnace output end 232 at a given draw speed as newly formed fiber 202. The newly drawn fiber 202 runs around pinch wheel 270 and is taken up by and stored in take-up spool 280.

Example Preforms and Slotted PBG Fibers

Figure 9A:
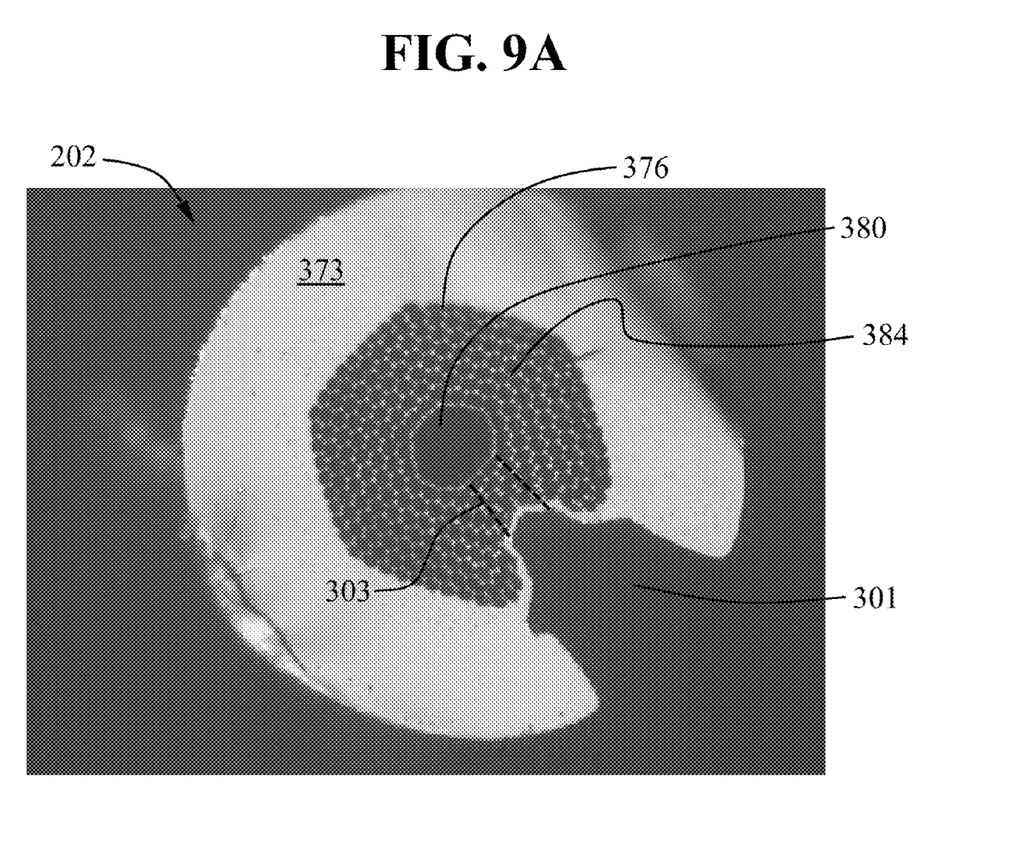
FIG. 9A is a cross-sectional photograph of an exemplary hollow-core, slotted PBG fiber formed using a PBG preform, wherein both preform slots were formed in a single operation by cutting through the cladding tube and part way into the PBG cane, but not into the PBG region.

FIG. 9A is a cross-sectional photograph of an exemplary fiber 202 formed using PBG preform 10 as described above, wherein the PBG preform slots 40 and 100 were formed in a single operation by cutting through cladding tube 20 and part way into PBG cane 60, but not into PBG region 76. The procedure used a 3 mm wide diamond-bonded wheel to grind slot 40 to length $L_1$ of about 4 inches and at distance $D_1$ of about 1 inch from cladding tube front end 30. Slot 100 was also ground in PBG cane 60 from cane front end 70 to length $L_2$ also about 4 inches long and to a depth such that slot bottom 110 was located above one of the flat sides 77 of PBG region 76 by distance $D_2$ of about 0.062 inches (see, e.g., FIG. 2).

Figure 9B:
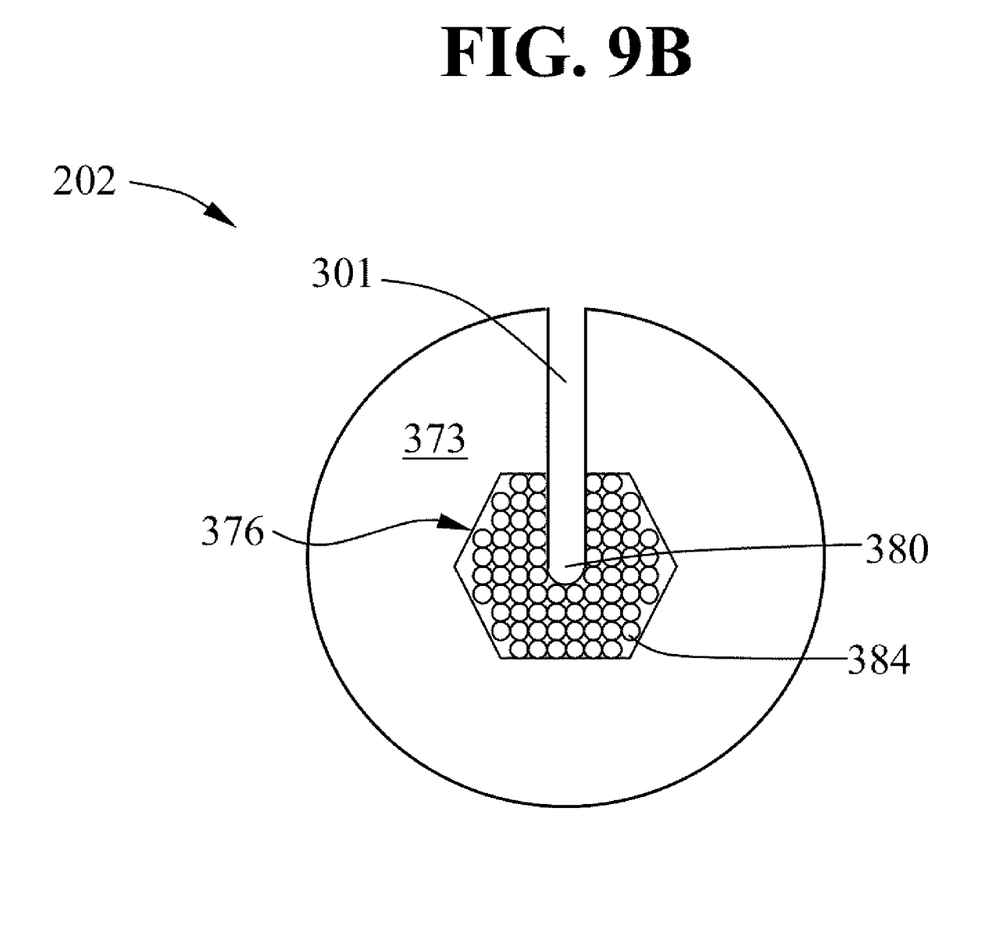
FIG. 9B is a cross-sectional schematic diagram illustrating an exemplary embodiment of a finalized hollow-core, slotted PBG fiber, wherein the slot connects with the hollow core.

The resulting fiber 202 has an outer cladding region 373 that surrounds a PBG region 376 having a hollow core 380. Outer cladding region 373 corresponds to merged cladding tube 20 and cane outer region 72 (or to "pre-merged" cladding region 73) of preform 10. Preform slots 40 and 100 also merge to form a single, elongated side opening or slot 301 that extends into PBG region 376. In an exemplary embodiment where PBG region 76 includes air holes 84, PBG region 376 includes corresponding air holes 384. FIG. 9B is a cross-sectional schematic diagram illustrating an exemplary embodiment of a finalized fiber 202 wherein slot 301 connects with hollow core 380.

The present invention is directed to forming fiber 202 using either a one-step or a two-step process. In the one-step process, slot 301 is formed during the drawing process so that it connects with hollow core 380. This creates a fire-polished slot without the creation of mechanically created debris. In the two-step process, slot 301 does not initially reach hollow core 380 during the fiber draw, and a second process (e.g., a machining process such as a grind process or a laser process) is used to connect (e.g., extend) the slot to the hollow core. While the second process can produce mechanical debris, the amount thereof is less than that created by having to machine slot 301 starting from cladding tube outer surface 26.

Slot 301 of fiber 202 of FIG. 9A forms a "nineteen-hole" defect, i.e., nineteen holes are missing from PBG region 376. Slot 301 in FIG. 8 is then extended (e.g., via precision machining or laser processing) to connect with hollow core 380 as indicated by the dashed lines 303. In an exemplary embodiment, the laser process includes using a pulsed femtosecond laser to ablate the material between slot 301 and hollow core 380. In an exemplary embodiment, the thickness of the material to be removed is between about 20μ to 35 μm. The material to be removed includes a portion of PBG region 376 and may also include a portion of outer cladding region 373, depending on the depth of slot 301. In an exemplary embodiment, fiber 202 is held in a V-groove fixture via vacuum assist, and the fixture is moved past the femtosecond-pulsed laser beam in a manner that controls the ablation rate.

It is noted here that forming slot 301 and then extending the slot to reach hollow core 380 results in fiber 202 that is stronger (i.e., has a greater tensile strength) by a factor of about 2× or more than a slotted fiber created by forming the slot directly through the outer cladding region 373. The reflow of the fiber structure that occurs when forming slot 301 by drawing preform 10 serves to reduce the formation of flaws that can undermine fiber strength. In particular, it creates a smooth groove surface and reduces point defects, thereby contributing to the formation of a stronger fiber 202.

Figure 10:
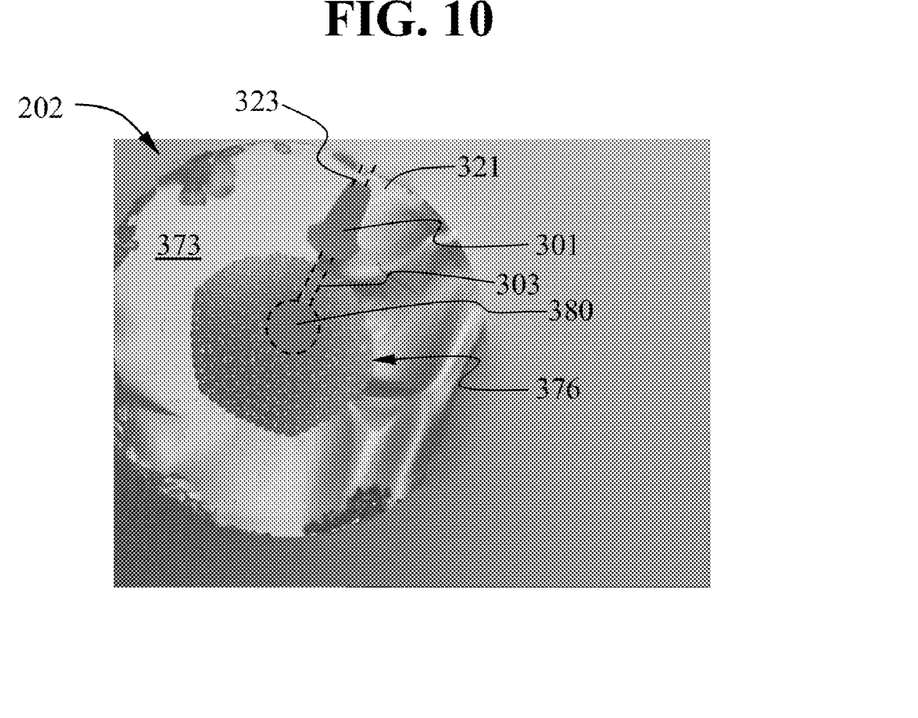
FIG. 10 is a cross-sectional photograph of an exemplary hollow-core, slotted PBG fiber formed using a PBG preform, wherein the slotted cladding tube was surrounded by a thin, non-slotted cladding tube so as to form a covered slot (301) in the drawn fiber.
Figure 11:
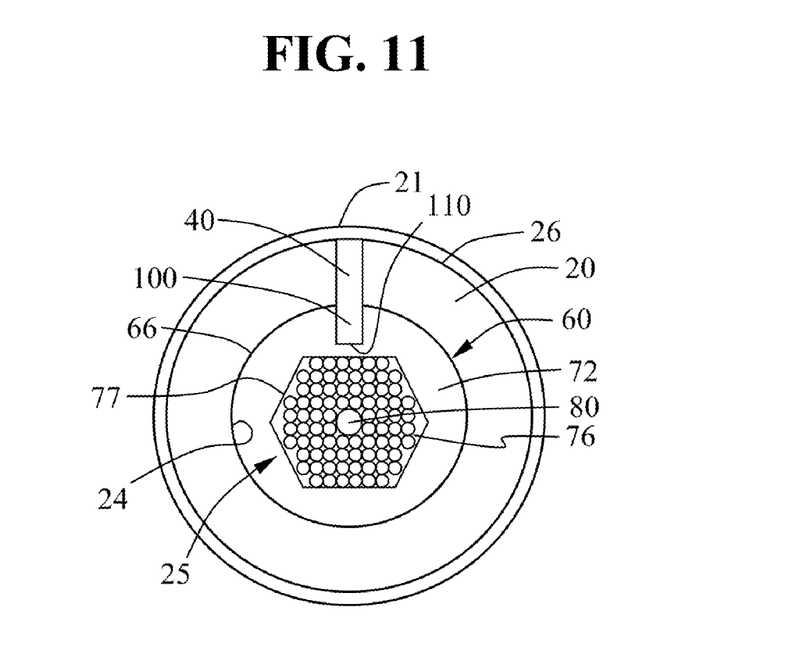
FIG. 11 is a cross-sectional view of the preform used to form the slotted PBG fiber of FIG. 10.

FIG. 10 is a cross-sectional photograph of an exemplary fiber 202 formed using a PBG preform that is similar to preform 10 described above, but wherein slotted cladding tube 20 was surrounded by a thin, non-slotted cladding tube 21 as shown in the preform illustrated in FIG. 11. In this instance, slot 301 formed in the resulting fiber 202 is covered by a thin glass layer 321, thereby forming a "covered slot" or "channel." Such a covered slot 301 is useful for sensor applications that benefit from trapping the target substance to be measured.

In an exemplary embodiment, covered slot 301 is connected to a pressure and/or vacuum system during the drawing process to control the size of the slot, the thinness of glass layer 321, and to form a marker to indicate where the slot resides within the fiber 202 by adding enough pressure to the slot such that the fiber bulges in the thin-walled area.

In another exemplary embodiment, one or more holes 323 are made in thin glass layer 321, and slot 301 is extended (via holes 303) through to hollow core 380 so that a target substance (discussed below) can enter covered slot 301.

Figure 12:
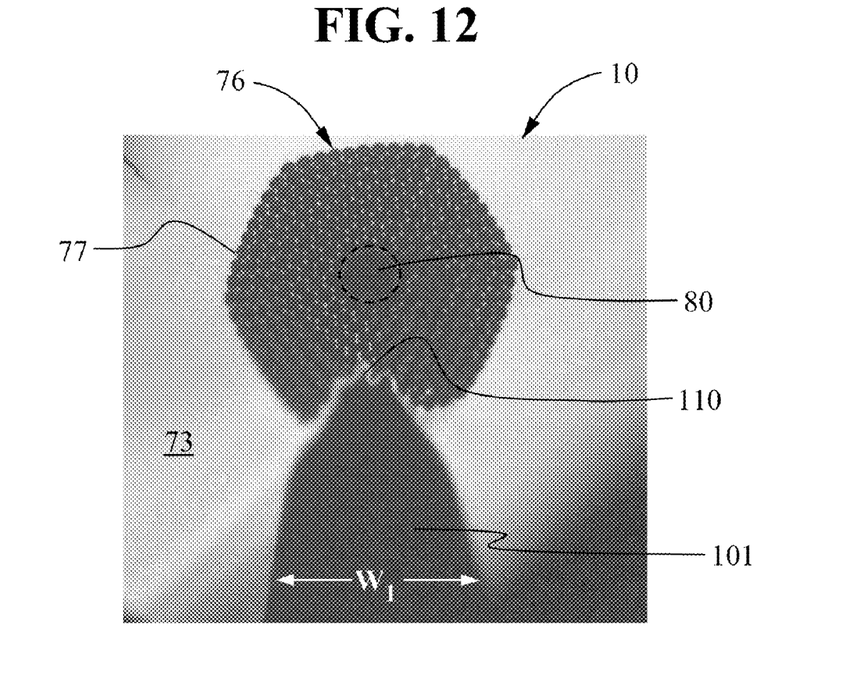
FIG. 12 is a cross-sectional photograph of an exemplary PBG preform wherein the preform was processed to form a unitary structure prior to forming the respective preform slots by performing a single grinding operation.

FIG. 12 is a cross-sectional photograph of an exemplary PBG preform 10 wherein the preform was processed (e.g., drawn or "pre-drawn") to merge cladding tube 20 and PBG cane 60 into a unitary structure prior to performing a single machining (e.g., grinding) operation to form slots 40 and 100 as single slot 101. The resulting slot 101 has nominal width $W_1$ of 0.065 inches, though it has a taper at bottom 110 due to the nature of the machining operation. Note also that in this embodiment, bottom 110 of slot 101 falls within PBG region 76, as is shown in FIG. 3 discussed above. Note also that the interface between cladding tube 20 and PBG cane 76 is eliminated by drawing preform 10 prior to drawing fiber 202 from the preform, as discussed above in connection with FIG. 7.

The relatively narrow slot 100 reduces the deformation of PBG region 76 during the drawing process by decreasing the amount of heat that is allowed to reach the PBG region during the drawing process. This approach to slot formation eliminates the need to align cladding and cane slots 40 and 100 and substantially eliminates slot deformation that occurs when an interface exists between cladding tube 20 and PBG cane 60.

An advantage of using a slotted PBG preform 10 to form fiber 202 is that the resulting fiber is likely to be stronger than a PBG fiber having a slot machined into it after the drawing process. This is because slot 301 is "flame-polished" during the drawing process, whereas the post-draw machining process on the fiber tends to disrupt the microstructured lattice and leave a roughened slot. In addition, even if a machining process is required to connect slot 301 to hollow core 380, the outer edges of the slot remain smooth.

Environmental Sensor

As discussed above, fiber 202 is suitable for use as a sensor because slot 301 allows a target substance (gas, liquid, particulate, etc.) from the surrounding environment to interact with at least one core mode propagating in hollow core 380. In an exemplary embodiment, hollow core 380 and slot 301 form a ridge waveguide wherein a portion of the guided light travels within the slot and another portion travels within the hollow core, thereby allowing the light to interact with the target substance within the slot as well as within the hollow core (to the extent that the target substance enters the hollow core). Slot 301 reduces the time required for the target substance(s) in the environmental atmosphere to interact with light guided by fiber 202, thereby decreasing the response time needed to sense the environment.

Figure 13:
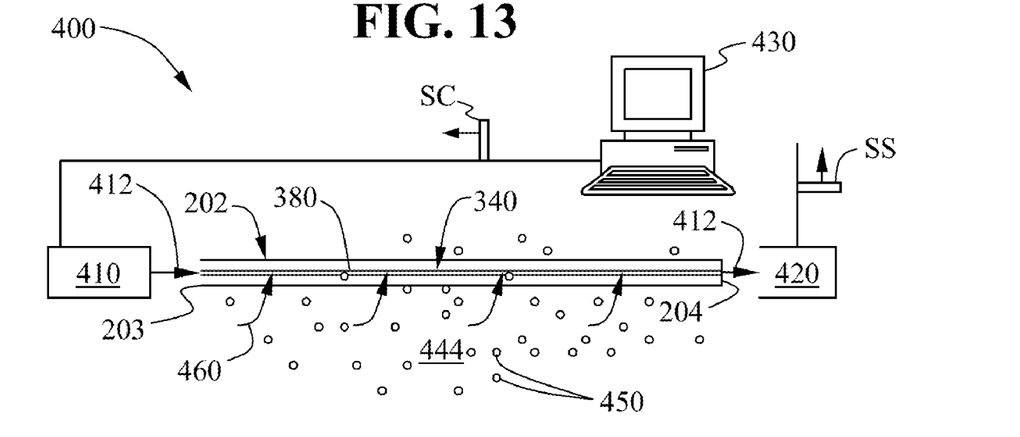
FIG. 13 is a schematic diagram of an exemplary embodiment of an optical waveguide environmental sensor that uses the hollow-core, slotted PBG fiber of the present invention.

FIG. 13 is a schematic diagram of an exemplary embodiment of an optical waveguide environmental sensor 400 that uses fiber 202 of the present invention. Sensor 400 includes a section of fiber 202 having a front end 203 and a back end 204. Sensor 400 also includes a light source 410 that emits light 412 and that is optically coupled to hollow core 380 at front end 203 of fiber 202. Light source 410 may include, for example, a quasi-monochromatic laser source, multiple laser sources (co-propagating or counter-propagating), a broadband light source (such as a tungsten halogen lamp, a glow bar, a spectral lamp, etc.), light-emitting diodes, or any other source that is used in sensing applications.

Sensor 400 also includes a light sensor 420 optically coupled to core 380 at back end 204 of fiber 202 and that is also connected to a controller/digital processor 430. Light sensor 420 may be, for example, a photodetector such as a phototransistor.

In the operation of sensor 400, at least a portion of fiber 202 (and preferably the entire fiber) is placed in an environment 444 that includes at least one target substance 450. Controller/digital processor 430 provides a control signal SC to light source 410 that causes the light source to emit light 412. The emitted light 412 is coupled into and propagates down hollow core 380 as well as down slot 301. Meanwhile, ambient target substance 450 is allowed to flow into slot 301, as indicated by arrows 460. A frequency of light 412 (for example, laser light) is selected to be affected by (e.g. scattered or absorbed by) target substance 450 so that its amplitude is reduced as compared to the case wherein there is no target substance in slot 301. For example, if sensor 400 is used as a fire detector, then the frequency of light 412 affected by target substance 450 may be selected to be one that is absorbed by carbon dioxide or a select by-product of the type of fire hazard contemplated.

Because target substance 450 affects at least some of light 412 traveling in slot 301 and hollow core 380, the amplitude of the light is diminished at fiber output end 234 as compared to the case wherein there is no target substance present in the slot.

Light sensor 420 receives light 412 that exits fiber 202 at back end 234 and generates an electrical signal SS that is representative of the amount of the light detected. Controller/digital processor 430 receives electrical signal SS and continuously monitors the amplitude of this electrical signal. Controller/digital processor 430 is programmed such that when the amplitude of electrical signal SS falls below a select threshold because a certain amount of target substance 450 is present in slot 301 and hollow core 380, the controller/digital processor (or another circuit, not shown) triggers an alarm.

Because slot 301 provides nearly immediate access to target substances, the response time of sensor 400 is almost immediate. In addition, because of the relatively low losses associated with the optical ridge waveguide formed by hollow core 380 and slot 301, the length of the section of fiber 202 may be on the order of 10 meters or more. This results in sensor 400 having high sensitivity and allows it to broadly sample ambient target substances present in a particular area, which reduces the chances of false positives and thereby enhances the overall reliability of the sensor.

It will be apparent to those skilled in the art that various modifications and variations can be made to the present invention without departing from the spirit and scope of the invention. Thus, it is intended that the present invention covers the modifications and variations of this invention provided they come within the scope of the appended claims and their equivalents.

What is claimed is:

1. A preform for forming a slotted photonic band-gap (PBG) optical fiber, comprising:
   a cylindrical cladding tube having a first central axis, a front end, a back end, an inner surface that defines an open interior, and an outer surface, the cladding tube having a first longitudinal slot formed in the outer surface through to the inner surface and having a front end and a back end;
   a cane having a second central axis, a PBG region arranged along the second central axis and having a hollow core substantially centered on the second central axis, and a solid outer region surrounding the PBG region and having an outer surface, the cane having a second longitudinal slot formed in the solid region outer surface; and
   wherein the cane is disposed within the cladding tube interior with the first and second central axes substantially aligned and with the first and longitudinal second slots substantially aligned.

2. The preform of claim 1, wherein the second longitudinal slot extends to the cane front end.

3. The preform of claim 1, wherein the first longitudinal slot does not extend to the cladding tube front end.

4. The preform of claim 1, wherein the first longitudinal slot has a width $W_1$, the second slot has a width $W_2$, and wherein $W_2 \geq W_1$.

5. The preform of claim 1, wherein the second longitudinal slot extends into the PBG region.

6. The preform of claim 1, wherein the second longitudinal slot extends into the hollow core.

7. The preform of claim 1, further comprising a thin, non-slotted cladding tube surrounding the slotted cladding tube.

* * * * *